US008523568B2

(12) United States Patent
Heo

(10) Patent No.: US 8,523,568 B2
(45) Date of Patent: Sep. 3, 2013

(54) DENTAL IMPLANT

(75) Inventor: Young Ku Heo, Seoul (KR)

(73) Assignee: Neobiotech Co., Ltd. (KR)

( * ) Notice: Subject to any disclaimer, the term of this patent is extended or adjusted under 35 U.S.C. 154(b) by 0 days.

(21) Appl. No.: 13/207,582

(22) Filed: Aug. 11, 2011

(65) Prior Publication Data

US 2011/0300510 A1 Dec. 8, 2011

Related U.S. Application Data

(63) Continuation of application No. PCT/KR2010/000686, filed on Feb. 4, 2010.

(30) Foreign Application Priority Data

Feb. 24, 2009 (KR) .................. 10-2009-0015155

(51) Int. Cl.
A61C 8/00 (2006.01)
(52) U.S. Cl.
USPC .......................................... 433/174
(58) Field of Classification Search
USPC ................ 433/172–176, 201.1, 202.1, 215, 433/220, 221; 623/16.11
See application file for complete search history.

(56) References Cited

U.S. PATENT DOCUMENTS

| 5,417,568 A * | 5/1995 | Giglio ........................... 433/173 |
| 5,967,783 A | 10/1999 | Ura |
| 7,137,817 B2 * | 11/2006 | Mena ............................ 433/174 |
| 2002/0081553 A1 * | 6/2002 | Tramonte ...................... 433/173 |
| 2005/0153261 A1 * | 7/2005 | Chang .......................... 433/173 |
| 2010/0009316 A1 * | 1/2010 | Hurson ......................... 433/173 |

FOREIGN PATENT DOCUMENTS

| JP | 2008-245994 A | 10/2008 |
| KR | 10-2005-0090651 A | 9/2005 |
| KR | 10-2007-0119802 A | 12/2007 |

OTHER PUBLICATIONS

International Search Report (PCT/KR2010/000686).

* cited by examiner

Primary Examiner — Heid M Eide
(74) Attorney, Agent, or Firm — Park & Associates IP Law, P.C.

(57) ABSTRACT

A dental implant of the invention allows an immediate masticatory function just after being implanted in a bone structure, does not need a secondary operation, and can be effectively applied even in thin and short alveolar bone. The dental implant comprises a body portion to be inserted in the bone structure and a mounting portion integrally formed on the body portion, the body portion including a thin and short core, screw blades formed along an outer peripheral surface of the core in the shape of a wide and deep screw, and a connecting portion formed in the shape of a plurality of vertical holes and grooves and capable of containing bone growth factors. The mounting portion has a gum adhering portion to protect bone tissues and a post to be mounted with an abutment or a prosthesis thereon.

17 Claims, 5 Drawing Sheets

DENTAL IMPLANT

REFERENCE TO RELATED APPLICATIONS

This application claims priority to PCT/KR2010/000686 filed on Feb. 4, 2010, which designates the United States and claims priority of Korean Patent Application No. 10-2009-0015155 filed on Feb. 24, 2009, the entire contents of which are incorporated herein by reference.

FIELD OF THE INVENTION

The present invention relates to a dental implant implanted in an upper portion of alveolar bone within the oral cavity. More particularly, the present invention relates to a dental implant that may relatively quickly perform its functionality within a relatively short period of time compared to a conventional implant, may decrease damage to the alveolar bone, and may effectively cope with formation of the alveolar bone.

BACKGROUND OF THE INVENTION

An implant corresponds to a structure that is to be implanted in a bone of a living body for the purpose of treatment. The implant may be used when mounting a prosthesis on the alveolar bone instead of a lost tooth and may also be used when replacing an articular joint of a human body.

A dental implant generally includes an implant body (hereinafter, an implant), an abutment, and a prosthesis. The implant is implanted to a bone structure corresponding to an area where a tooth is lost within the oral cavity. In general, a screw spiral is formed along the outer peripheral surface of the implant. Also, the abutment is tightened to an upper portion of the implant to support the prosthesis that is substantially provided in a tooth shape.

The dental implant is referred to as an osseointegration implant in which the osseointegration is completed. The osseointegration corresponds to a state where a migration is barely observed with bare eyes since the implant surface and newly formed bone tissue directly contact with each other immediately after implantation without biologically having the interposed soft tissue. It generally takes three to six months to complete the above osseointegration after implanting the implant. It is known that the osseointegration should be sufficiently achieved before an occlusion force is applied. When the external force is applied in a state where the sufficient osseointegration is not achieved, the implant surface and the bone structure may not directly contact with each other and, instead, soft tissue may be interposed therebetween, which may result in the failure of osseointegration, that is, the failure of implant. Accordingly, in the case of the conventional implant, it is general not to apply the masticatory pressure to the implant for a predetermined period of time, for example, three to six months after implantation so that sufficient osseointegration may be performed for the outer screw surface of the implant and the bone tissue around the surface.

Human beings have various types of alveolar bones. In many cases, the length and the width of available alveolar bone may be sufficient and osseous tissue may be strong. On the other hand, the length of available alveolar bone may be short or significantly thin. When a tooth is unattended after its extraction for a long period of time, or when a tooth is extracted due to serious gum disease, the alveolar bone may be significantly damaged and only short and thin alveolar bone may remain. In this case, a long implant may not be implanted. For example, in many cases, inferior alveolar nerve and blood vessel pass a lower portion of a tooth portion of a lower jaw, maxillary sinus exists in a tooth portion of an upper jaw, and nostrils exist close to a densincisvus portion of the upper jaw. In this case, when the long implant is to be implanted, a vertically sufficient bone graft may need to be implemented to implant the long implant. The vertical bone graft is difficult and has a very low success rate. A conventional short implant has an insufficient capability for enduring an occlusion force and thus, more implants may need to be implanted and need a longer waiting period than the long implant and thus, may easily fail due to a weak force against the occlusion force.

In a case where an upper portion of alveolar bone is thin, when a conventional implant with a small diameter is implanted to prevent the exposure of the implant, the implant may not endure the occlusion force, thereby causing implant fracture. To prevent the fracture, an implant with a large diameter needs to be implanted. However, when the alveolar bone is thin, a horizontal bone graft operation may be performed to minimize a probable future bone loss. Compared to the vertical bone graft operation, a success rate of the horizontal bone graft operation is relatively high. However, the horizontal bone graft operation may cause greater pain and require long operation time in a patient side and may be hard on a dentist side.

FIG. 1 illustrates a sectional view of a conventional implant 10.

Referring to the conventional implant 10 of FIG. 1, from a distal portion, an end portion of bone tissue of the implant 10, to a proximal portion, a uppermost portion of a body portion to be inserted in bone tissue, a valid diameter of the implant 10 gradually increases or is uniformly maintained and the implant 10 has a maximum diameter in at least the proximal portion. The proximal portion has the largest diameter in order to prevent the implant fracture from occurring in the proximal portion, to prevent the implant from continuously entering the bone tissue when implanting the implant, and to prevent the abutment from loosened.

However, as shown in FIG. 1, an upper portion of the alveolar bone is generally thin and thus, the implant may be externally exposed from the bone structure of the alveolar bone while the implant is implanted or only the thin bone may remain around the proximal portion. In this case, when a prosthesis is installed, a force against an external force may decrease and a greater force may be concentrated on the alveolar bone whereby a bone loss may further quickly occur.

To maintain a bone of the proximal portion is an important factor to guarantee a long-term success of the implant. When the bone fracture continuously occurs in the proximal portion, the proximal portion contained in bone tissue may be gradually exposed. In this case, even with respect to the same occlusion force, a further greater force may be concentrated on an area where the bone fracture has occurred whereby the implant may not endure the occlusion force and the implant may be fractured in this area. Accordingly, it becomes an important issue to maintain the bone of the proximal portion for a long period of time.

Important factors affecting the bone loss in the proximal portion of the implant may include a thickness of bone wrapping around the upper portion, a connection method of the upper portion, and the like.

First, it may be safe when the thickness of bone tissue wrapping around the proximal portion of the implant is to be minimum 1.5 mm-2 mm towards a side. When the thickness of bone tissue becomes to be smaller than 1.5 mm-2 mm, the bone loss may easily occur. As described above, the upper portion of alveolar bone unattended for a long period of time after extraction of a tooth may be thinned. In this case, when the implant of which the diameter of the proximal portion is large is implanted, the bone loss may occur. Therefore, in many cases, a difficult bone graft may need to be accompanied to reinforce the thickness of alveolar bone. Accordingly, if possible within the strength of enduring the occlusion force, the implant of which the diameter of the proximal portion is small may be advantageous to prevent the bone loss.

Second, among the important factors affecting the bone loss in the proximal portion of the implant, corresponds to the method of connecting the proximal portion and the abutment. An integral type in which the implant and the abutment are integrally formed with each other is most safe and has advantages in that a relatively small bone loss occur, a secondary operation is not required, and there is no need to separately connect the abutment. However, in the case of the integral type, the long abutment is exposed to be above the gum and thus, needs to be cut to be suitable for the direction and the length immediately after implantation. In addition, a prosthesis needs to be mounted thereon immediately after implantation. Since the masticatory pressure may be applied immediately after implantation, the weakly implanted implant may easily fail. Accordingly, the integral type is not widely used.

Accordingly, a submerged or non-submerged implant in which the implant and the abutment are separate from each other has been developed. The submerged or non-submerged implant has advantages in that it is safe since the implant can be buried in the gum until the implant is sufficiently adhered to the bone tissue and there is an opportunity of selecting an optimal abutment for the prosthesis. Due to the above reasons, the submerged or non-submerged implant is currently most widely used. However, even the submerged or non-submerged implant still needs the secondary operation in many cases and needs to form a connecting groove within the proximal portion of the implant in order to later connect the abutment to the implant. Therefore, due to the empty inside, the strength may be weakened and the proximal portion may need to be maintained to have a possibly large diameter. In the case of the submerged or non-submerged implant, it is difficult to decrease the diameter of the proximal portion and the inside structure is weak, thereby causing continuous implant fracture by an occlusion force. Also, due to a micro-gap of the connecting portion, the bone loss may increase.

A circumstance where a patient has to make a living for a long period of time without a tooth may bring a mental and physical pain to the patient. In many cases, the patient may not make a normal social life. Accordingly, there is an increasing need for an implant that may reduce a post-operation pain by simplifying an operation if possible, may minimize the aftereffect, and enables a tooth recovery as soon as possible after the operation, thereby enabling a masticatory function, enabling a patient to return to a previous normal social life, and promising a long-term success.

SUMMARY OF THE INVENTION

The present invention provides a short implant that may be successfully implanted without a vertical alveolar bone graft even when osseous tissues are weak or when vertically very short bone mass remains.

The present invention also provides a dental implant that may provide a sufficient bearing power while an outer diameter of an implant body is relatively small compared to a conventional implant and a section size thereof decreases.

The present invention also provides a dental implant that may be implanted without the need for a vertical bone graft even in a narrow and thin bone structure, and also provides a dental implant that may not be unnecessarily exposed in correspondence to the shape of an alveolar bone having a narrow upper portion and may be rapidly recovered from damage to the alveolar bone.

The present invention also provides an implant that enables a long-term bone maintenance without losing a bone of a proximal portion, an upper portion of an implant body.

The present invention also provides an implant that may need only a one-time operation without the need for a secondary operation and may also be enables an osseous-integrated in a bone of a living body with a sufficient bearing power.

The present invention also provides an implant that may prevent necrosis from occurring in a bone structure contacting with an implant after implanting the implant thereon.

The present invention also provides an implant that enables new bone tissues to be quickly formed around the implant surface after implanting the implant thereon.

The present invention also provides an implant that may satisfy all the above criteria and may be successfully implanted even though an artificial tooth is mounted thereon immediately after implantation, and may exhibit an excellent fixing force capable of enduring an occlusion force, and also provides an implant that may reduce at least an osseointegration time between the bone and the implant.

The present invention also provides an implant that may be a conventional integral implant in which an abutment is protruded within oral cavity, however, may be a non-submerged or one stage implant. Accordingly, compared to the conventional integral type, a mounting portion is not significantly exposed to be above gingiva and there is no need to modify a length or the shape of a connecting portion within the oral cavity.

According to an aspect of the present invention, there is provided a dental implant, an immediately functioning implant capable of providing a prosthesis thereon at any time after being implanted, the dental implant comprising a body portion to inserted in a bone structure and a mounting portion integrally formed on an upper portion of the body portion, the body portion including a thin and short core and screw blades formed along the outer peripheral surface of the core in the shape of a wide and deep screw, and connecting portions formed with a plurality of holes or grooves that may vertically pass through the circumference of the screw blades and contain bone growth factors. An outer diameter of a proximal portion, an uppermost portion of the body portion, gradually decreases from a center portion, a maximum diameter of the body portion, to the proximal portion. The mounting portion has a gum adhering portion to protect bone tissues and a post to be mounted with an abutment or a prosthesis thereon.

The screw blades may be formed along the outer peripheral surface of the core. In this instance, it is possible to decrease the diameter of the screw blades to be relatively small around the proximal portion. Also, it is possible to prevent the screw blades positioned in the upper portion of the alveolar bone from being exposed out of the alveolar bone when the implant is implanted in the alveolar bone.

The wide and deep screw blades in the shape of a screw may be provided around the core of the body portion to be inserted in the bone structure. Even though the screw blades may be provided in the shape of a general triangular screw that is formed on the outer peripheral surface of the core, the screw blades may have a section capable of increasing bone mass between blades, and forming the vertical contact surface between the blade surface and the bone surface to be wide by forming a thin structure like the blade. The screw blades may be formed in the shape of a single screw. Like double screw spirals, a plurality of screw blades may be formed on the outer peripheral surface of the core.

The wide and deep screw blades may be supported by the bone structure on the wide surface and thus, provide a strong bearing power. Also, since the screw blades are formed in the shape of blades, a total volume of the blades may decrease. Accordingly, when implanting the implant, an amount of bone cut for blade insertion may decrease whereas the bone mass for supporting the implant may increase.

Since the screw blades are wide and deep compared to a conventional screw spiral, the bone structure between screw blades after implanting the implant may be mostly isolated and thus, the blood supply may not be smoothly performed. As a result, the side effect such as bone necrosis and the like may occur in the bone structure. To foster the bone formation and the osseointegration by preventing the bone necrosis, and by enabling the smooth blood supply, the connecting portions may be formed to partially vertically pass through the screw blades and thereby enables communication. The connecting portions may be provided to the screw blades in the shape of a plurality of grooves or holes. Since vertically positioned bones or tissues may communicate with each other via the connecting portions, regeneration or recovery of bone or tissue may be further quickly achieved.

Depending on embodiments, a bone growth factor such as bone morphogenic protein (BMP) may be provided on or be injected to the connecting portion, and may further accelerate formation of new bone tissues after implanting the implant.

In particular, in the case of an integrated typed implant in which the mounting portion and the core are integrally formed with each other, an inner hole for a screw is not formed in the core. Therefore, it is possible to form the core to have a small diameter. Instead, by forming wide screw blades, it is possible to secure the sufficient bearing power. In addition, as described above, while gradually decreasing the diameter of the screw blades in the proximal portion adjacent to the mounting portion, it is possible to suppress the screw blades from being exposed out of the alveolar bone. Also, depending on embodiments, the same effect may be achieved by decreasing the diameter of the proximal portion of the body portion to be smaller than the maximum diameter portion corresponding to a center portion of the body portion.

The integral typed implant has advantages in that the fracture probability is relatively small even though the diameter of the core in the proximal portion is reduced, and the blade capable of providing a strong bearing power may be formed on the proximal portion even though the screw blades has a decreasing diameter with getting closer to the proximal portion. Since the diameter of the core is relatively small, drilling for bone drilling may be minimized, thereby reducing an operation time. The wide blades may increase the bone bearing power compared to the conventional implant having the same diameter and the same length. On the contrary, according to an embodiment of the present invention, there may be provided an implant with a further shorter diameter to support the same occlusion force.

In the conventional implant, a screw mounting an abutment to the implant has a diameter of at least 2.0 mm irrelevantly to an external type and an internal type whereby the implant is formed to have a diameter of minimum at least 4.0 mm. However, in the case of the dental implant according to an embodiment of the present invention, since a screw hole is absent in the proximal portion, it is possible to reduce the diameter of the core and to form the deep screw blades within the same diameter, thereby increasing a bone support area in this portion. More specifically, in the conventional regular implant of which the maximum diameter is 4 mm, the diameter of the proximal portion is 4 mm and the diameter of the core in the proximal portion is also 4 mm. On the other hand, in the regular implant of the present invention, the diameter of the proximal portion including the screw blades may be reduced to be smaller than 4 mm, for example, 3.8 mm-2.5 mm and the diameter of the core in the proximal portion may also be reduced to be smaller than 3.8 mm-2.0 mm. This aspect may provide an important element that it is possible to successfully implant the implant without bone graft even in a relatively narrow upper portion of the alveolar bone.

Also, in the conventional regular implant of which the maximum diameter is 4 mm, the maximum diameter of the screw blades is 4 mm and the diameter of the core is 3.2 mm-3.3 mm. On the other hand, in the regular implant of the present invention, the maximum diameter of the screw blades may be 4 mm which is the same as the conventional implant. However, it is possible to decrease the maximum diameter of the core to be 3 mm-1.5 mm. Accordingly, there may be provided the implant that may maximize a support area and a contact area with the bone even in the same outer circumference and may endure the masticatory pressure even though the implant is exposed thereto immediately after being implanted.

The implant of the present invention may be the conventional integral typed implant in which the mounting portion is protruded towards the oral cavity. Generally, the implant of the present invention may be a non-submerged integral typed implant. Therefore, according to an aspect of the present invention of the present invention, there is provided the implant in which the mounting portion is not protruded to be above the gum compared to the conventional integral typed implant and there is no need to transform the length or shape of the mounting portion within the oral cavity. In general, the mounting portion may employ a frictional type scheme. Also, the mounting portion may employ a cement-retained type scheme or a screw-retained type scheme and thus, is not limited to a mounting scheme between the mounting portion and the prosthesis.

According to an embodiment of the present invention, there may be provided an implant that may achieve various effects by mutually combining a short and thin core, wide and deep screw blades positioned around the core, connecting portions having a plurality of holes or grooves on the screw blades, a proximal portion with a small diameter, and a mounting portion integrally formed with the proximal portion.

For example, compared to the conventional implant, in the implant of the present invention, it is possible to reduce the diameter and the length of the core, which is attributed to aspects that the diameter of the core can be reduced due to the integrally formed body portion and mounting portion, and a sufficient bearing power can be secured due to the relatively wide screw blades even though the implant is short. The wide and deep screw blades may be supported from the bone structure on the wide surface. Therefore, even in the implant with the same diameter and the short length, the screw blades may provide a strong bearing power compared the conventional implant and enables a mastication function to be recovered within a relatively short period of time after implantation.

Also, in the case of the dental implant of the present invention, the diameter of the core is relatively small and the overall outer circumference including the screw blades gradually decreases from the center portion of the screw blades to the proximal portion. Therefore, the dental implant may be effectively implanted even in the alveolar bone where it is difficult to implant the conventional implant in which the core and the proximal portion have a relatively large diameter. That is, in the case of the dental implant of the present invention, even though the implant is implanted in the alveolar bone having a narrow upper portion, the implant may not be unnecessarily exposed. In addition, without vertical or horizontal bone graft, it is possible to maintain a necessary amount of alveolar bone around the proximal portion. Accordingly, it is possible to preserve or maintain the bone tissues of the upper proximal portion for a relatively long period of time, thereby extending a lifespan of the implant.

In addition, the connecting portions may be formed to vertically pass through the screw blades and the bone structure or blood tissues may perform mutual communication via the connecting portions. Accordingly, the rapid bone formation may be anticipated.

Also, it is possible to provide bone growth factors around the connecting portions and the core, and to enable the provided bone growth factors to remain there for a relatively long period of time after implantation. Therefore, the bone growth factors may induce new bone to be quickly formed on the implanted surface, may decrease an implant failure probability, and may help a function of the implant to be recovered soon.

Also, the mounting portion integrally formed with the core may achieve the following three effects.

First, as described above, since the mounting portion is integrally formed with the core, it is possible to reduce the diameter of the proximal portion.

Second, since the mounting portion is connected to the proximal portion in an integral form, a living body may not recognize, as an outside, a boundary between the proximal portion and the mounting portion and thus, may maintain the bone tissues of the proximal portion as is or may increase the bone tissues. In the case of a separate typed implant, due to the frequent separation and attachment of the abutment, the living body may recognize the boundary as the outside and thereby wrap the bone tissues with the soft tissues, which may result in losing bone tissues present in the upper portion of the proximal portion. Also, in the separate typed implant, micro-gaps may occur in the boundary between the abutment and the implant. Bacteria and toxin may leak out via the micro-gaps, thereby damaging the bone tissues of the proximal portion. Due to this reason, the implant of the present invention is provided as an integral type in which the mounting portion is integrally formed with a gum adhering portion to protect the bone tissues, and the implant has a soft tissue adhering portion capable of protecting the bone tissues between the prosthesis and the bone tissues, thereby minimizing the bone loss around the proximal portion. Third, according to an example of the present invention, the mounting portion is configured to provide a frictional typed abutment that is connected to the mounting portion. To avoid drilling or deformation within the oral cavity, a height of the mounting portion may be formed to be short to some extents, fitting for a height of gum. Through this, there is no need to unnecessarily grind the mounting portion immediately after implanting the implant. In addition, it is possible to readily determine when to mount the prosthesis thereon or when a mastication function is to be recovered after implantation. That is, when osseous tissues are weak and the bone graft is more performed, it is possible to connect only a healing abutment to be above the mounting portion and to wait for a predetermined period of time in a state where the mounting portion is not protruded to be above the gum and an external force is not applied, in order to delay a prosthesis mount time. When it is determined that a sufficient fixing power is obtained immediately after implantation and a function can be immediately recovered, it is possible to connect the abutment to the mounting portion immediately after implantation and mount the prosthesis thereon.

As described above, according to an embodiment of the present invention, even in a circumstance where it is difficult to perform an operation due to the short length, the weak osseous tissue, and the narrow upper portion of alveolar bone, the operation may be performed using the short implant without bone graft. In addition, a secondary operation may not be required and various types of upper prosthesis mounting methods may be employed. Since the bone tissues are maintained for a relatively long period of time, the implant may have an extended lifespan.

DETAILED DESCRIPTION OF THE INVENTION

Figure 1:
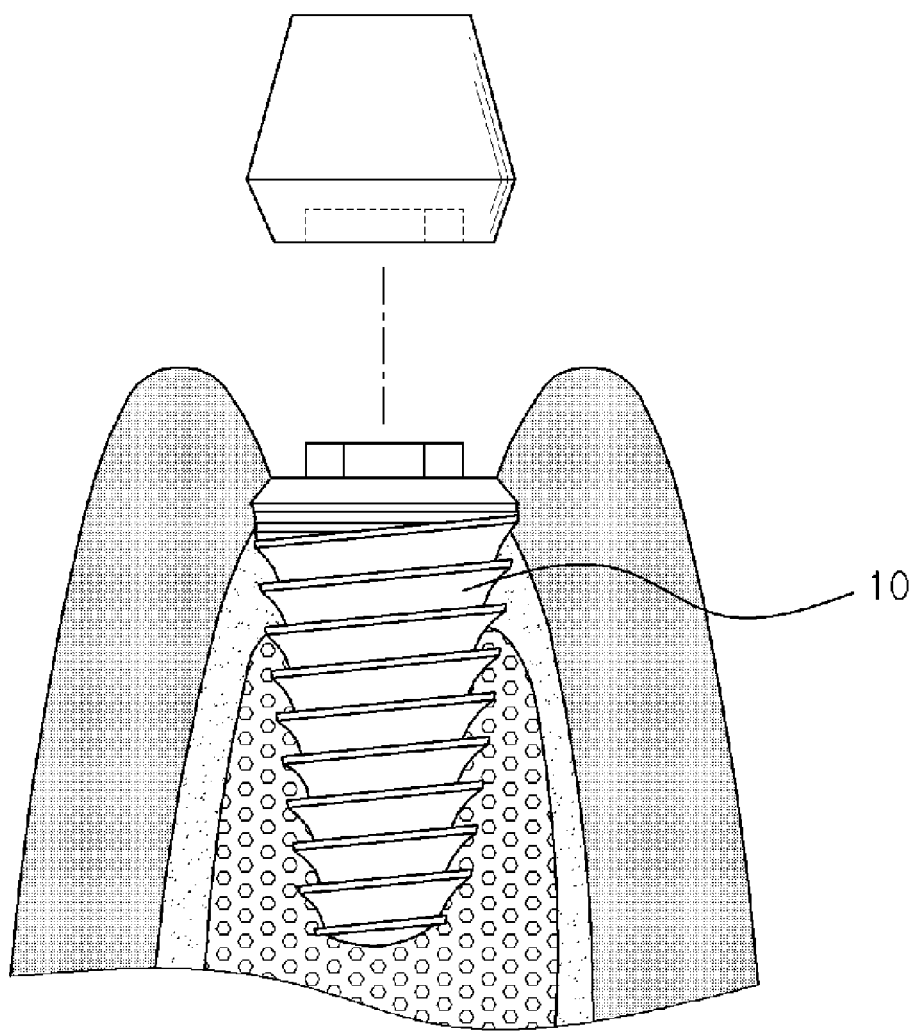
FIG. 1 is a sectional view illustrating a conventional implant.

Reference will now be made in detail to embodiments of the present invention, examples of which are illustrated in the accompanying drawings, wherein like reference numerals refer to the like elements throughout. The embodiments are described below in order to explain the present invention by referring to the figures.

Figure 2:
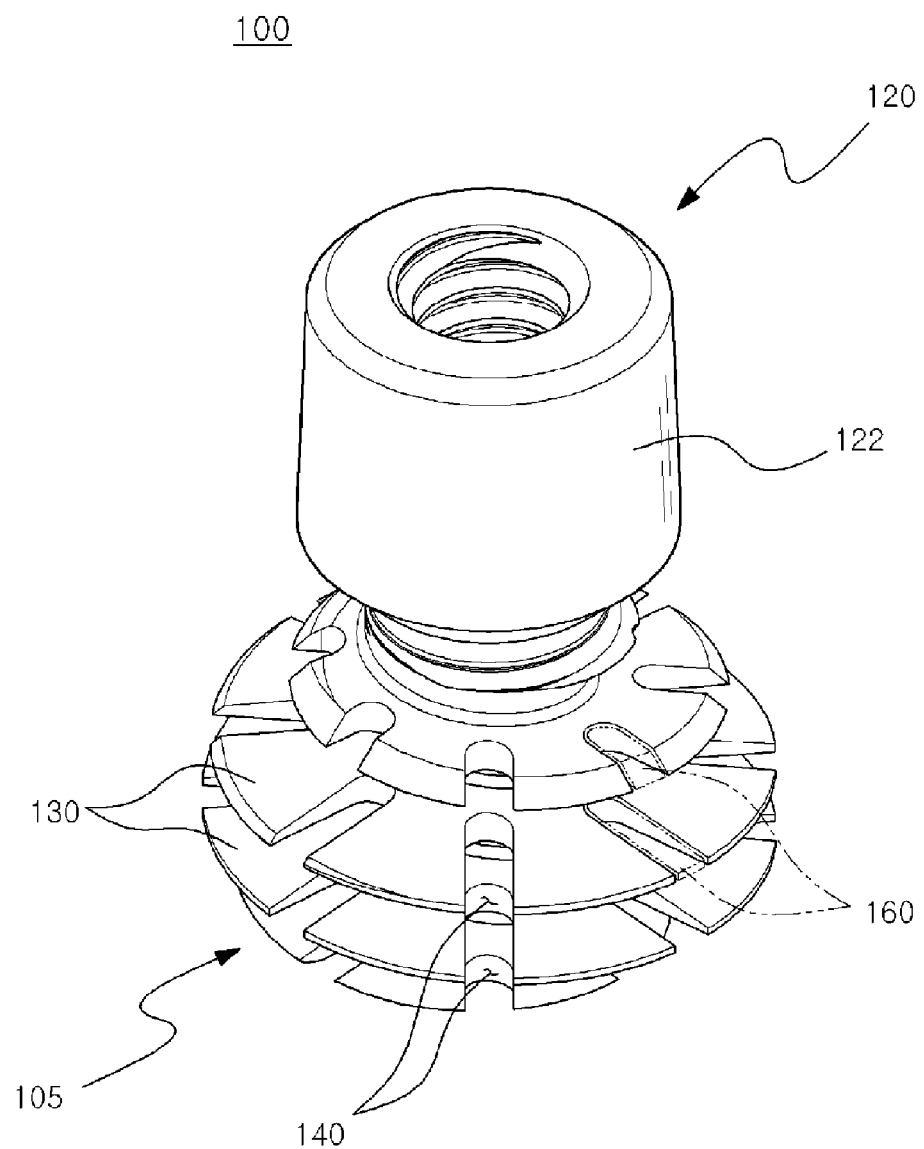
FIG. 2 is a perspective view illustrating an implant according to an embodiment of the present invention.
Figure 3:
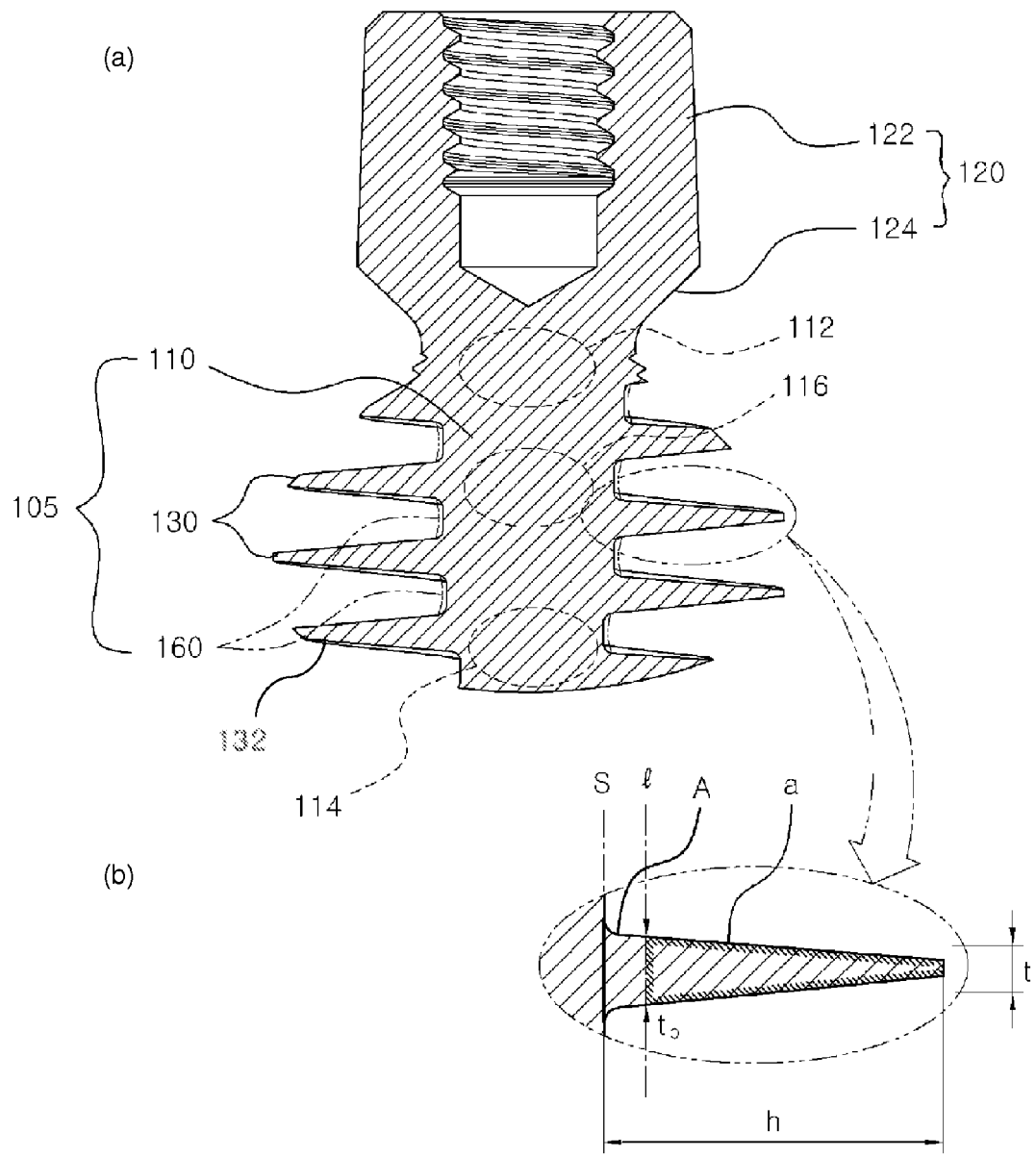
FIG. 3 is a sectional view illustrating the implant of FIG. 2.
Figure 4:
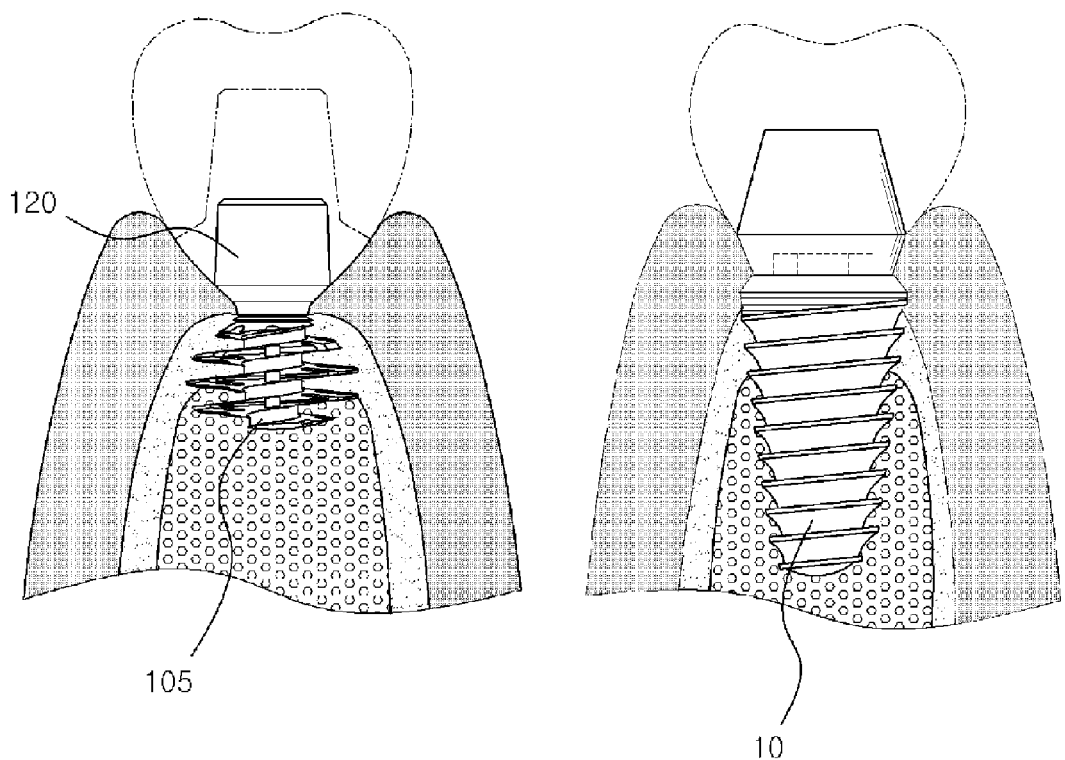
FIG. 4, parts (a) and (b), illustrate sectional views to compare a usage example of the implant of FIG. 2 and the conventional art.

FIG. 2 is a perspective view illustrating an implant 100 according to an embodiment of the present invention, FIG. 3 is a sectional view illustrating the implant 100 of FIG. 2, and FIG. 4, parts (a) and (b), illustrate sectional views to compare a usage example of the implant 100 of FIG. 2 and the conventional art.

Referring to FIG. 2 through FIG. 4, the implant 100 for a dental operation according to an embodiment of the present invention comprises a body portion 105 and a mounting portion 120. The body portion 105 and the mounting portion 120 are integrally formed with each other and may be formed using a bioaffinity material such as titanium, zirconium, and the like. The body portion 105 includes a core 110, screw blades 130, and connecting grooves 140. The mounting portion 120 includes a post 122 to be mounted with an abutment thereon and a soft tissue adhering portion 124 to adhere to soft tissue.

According to an embodiment of the present invention, the body portion 105 corresponds to a portion to be inserted in an alveolar bone, and the screw blades 130 are formed from a proximal portion 112, an upper end of the alveolar bone, to a distal portion 114, in the shape of the screw around the core 110.

The screw blades 130 may be formed to have a triangular section and, desirably, may be formed to have an approximately long rectangular section, and may be formed into the nearly right angle direction with respect to an axis of the core 110. According to another embodiment of the present invention, screw blades may be formed in a nearly rectangular shape with respect to an axis of a core and be gradually thinned to be in a triangular shape with getting closer to an end portion, or may be formed to be thinned gradually from a start portion.

Also, the screw blades 130 have a gradually decreasing diameter from an intermediate portion 116, a maximum diameter portion of the body portion 105, to the proximal portion 112. Accordingly, an upper portion of the screw blades 130 is formed to be narrowed. Compared to the conventional narrow implant of which a proximal portion is 3.5 mm, in a narrow implant of the present invention, it is possible to decrease a minimum diameter of the proximal portion up to 1.5 mm. In a regular implant of 4 mm, it is possible to decrease the minimum diameter up to 2.4 mm. Also, in a wide implant of 5 mm, it is possible to significantly decrease the minimum diameter up to 3 mm.

Referring to FIG. 4, when the implant 100 is implanted in the alveolar bone, the proximal portion 112 corresponding to an upper portion of the screw blades 130 may not be exposed from the core 110. Since the core 110 is relatively small, the upper portion of the alveolar bone may not be excessively pushed out from the alveolar bone. Also, loss of bone tissues occurring due to passing of the screw blades 130 may be quickly recovered (see part (a)). On the other hand, as shown in FIG. 1, in the conventional implant 10, the upper portion of the alveolar bone may be exposed out of the alveolar bone. Since the mounting portion between the implant and the abutment is adjacent to the bone structure, the bone loss may occur.

The body portion 105 may be formed to have a short length of, for example, 3 mm-12 mm and desirably, may be formed to have a length of 4 mm-8.5 mm. Even in this case, the body portion 105 may be stably mounted to the alveolar bone and the like. In addition, the core 110 may be formed to have a diameter of 7 mm or less and desirably, may be formed to have a diameter of 2 mm-4 mm.

Also, to decrease an amount of bone drilling and heat generation occurring in drilling a bone and to smoothen entering of the implant 100, the body portion 105 and the screw blades 130 may be formed to have a decreasing diameter with getting closer to the distal portion 114. In addition, without a change in the diameter of the core 110, only the screw blades 130 may be formed to have a gradually decreasing height with getting closer to the distal portion 114.

A cutting edge 132 may be formed on the screw blades 130 positioned around the distal portion 114, which is a structure required for self-tapping of the implant 100 in weak bone without bone drilling. However, since the screw blades 130 are generally wide and deep, it is recommended to perform pre-tapping for the screw blades 130 before implanting the implant 100.

A plurality of vertically passing connecting grooves 140 may be formed on the screw blades 130. The connecting grooves 140 may connect an upper space and a lower space blocked by the deep screw blades 130. The connecting grooves 140 enable vertically positioned bone tissues to partially communicate with each other and enable blood, required for healing a wound, to pass. Accordingly, it is possible to prevent necrosis of the bone tissues, deeply isolated between the deep screw blades 130 after implanting the implant, and to help the wounded bone tissues to be quickly recovered.

A cutting instrument may be employed to form the connecting grooves 140 on the screw blades 130, and grooves may be vertically concentrically formed by the cutting instrument.

Referring to FIG. 2, the thin and deep screw blades 130 may be formed to be supported by vertically or horizontally thick and deep bone mass. For this, a height h of the screw blades 130 from an outer peripheral surface s of the core 110 may be formed to be more than one fold of a thickness t of a lower portion. When the screw blades 130 are formed to be deep to some extents, the screw blades 130 may secure a sufficient bearing power even with a small diameter and it is easy to form the connecting grooves 140 on the screw blades 130. Also, when the screw blades 130 are formed to be too thin or wide, the strength may be degraded. Accordingly, the height h of the screw blades 130 may be formed to be less than three folds of the thickness of the lower portion t of the screw blades 130. According one preferred embodiment, the maximum height of the screw blades from the outer peripheral surface of the core is 0.6 mm-2.0 mm, and the thickness of a lower portion of the screw blades is 0.25 mm-1.5 mm.

Here, various concepts and methods may be employed to define the thickness t of the lower portion of the screw blades 130. For example, when a straight line l in parallel with the outer peripheral surface s is assumed based on an area A that is defined by a cross-section of the outer screw blades 130 from the outer peripheral surface s of the core s, and a sectional area a from an end of the screw blades 130 to the straight line l occupies 90% of a total sectional area thereof, a thickness $t_b$ of the lower portion of the screw blades 130 may be determined as an inner boundary thickness thereof based on the straight line l Bone growth factors 160 such as a bone morphogenic protein (BMP) may be provided on the connecting grooves 140, and the bone growth factors 160 may be provided even on the outer peripheral surface of the core 110 provided between the screw blades 130. The bone growth factors 160 may react with the adjacent bone or tissues after the implant 100 is implanted, and may enhance the recovery speed of the adjacent bone or tissue. By inwardly providing the bone growth factors 160 on the connecting grooves 140, it is possible to prevent the bone growth factors 160 from being pushed away by the bone or tissues and thereby peeled off. The bone growth factors 160 may remain for a relatively long period of time even after implanting the implant 100, and function to foster the bone formation.

The bone growth factors 160 may be provided on the screw blades 130 and also be provided on the outer peripheral surface of the core 110. When the bone growth factors 160 are provided on the core 110, it is possible to prevent the bone growth factors 160 from being peeled off during the implantation process by increasing a diameter of a drill bit to be greater than the diameter of the core 110 including the bone growth factors 160.

To implant the implant 100 in the bone structure and the like, drill bit holes may be formed in the bone structure in correspondence to the diameter of the core 110 and screw grooves may be formed in the bone using a screw groove forming instrument. Next, the implant 100 may be implanted in the bone structure. The bone growth factors 160 may be provided together when the implant 100 is manufactured, and may be provided on or injected to the connecting groove 140 before implanting the implant 100.

According to the present embodiment, the post 122 included in the mounting portion 120 is configured to be mounted with an abutment-prosthesis in the shape corresponding to the outer peripheral surface of the mounting portion 120 using a frictional type scheme.

A frictional typed post may be formed at an angle of 1°-4° and to have a length of 2 mm-7 mm at the same level as a height of gum. The combination of the angle and the length of the post may refer to a shape that is fixed by an appropriate pressure and is separable by a predetermined tension. The length of the mounting portion may correspond to a general gum height so that the mounting portion may not be drilled or be deformed within the oral cavity. When the mounting portion has the length at the same level as the height of gum, there is no need to unnecessarily grind the post immediately after implanting the implant. In addition, it is possible to readily determine when to mount the prosthesis thereon or when a mastication function is to be recovered after implanting the implant. Also, there is an opportunity for selecting a most idealistic abutment to be mounted to the mounting portion.

Even though the present embodiment describes the frictional typed post as an example, a cement-retained typed abutment or a screw-retained typed abutment may be integrally formed.

According to the present embodiment, the soft tissue adhering portion 124 of the mounting portion 120 corresponds to a short portion present between a lowermost boundary of the post 122, to be mounted with the abutment or the prosthesis thereon, and an uppermost end of the proximal portion 112 to be inserted in the bone tissues. Even though the length of the soft tissue adhering portion 124 is 0.3 mm-2 mm, it is desirable to form the soft tissue adhering portion 124 to have the length of 0.8 mm-1.3 mm. The soft tissue adhering portion 124 may be a mechanically processed smooth surface, or a slightly rough surface processed by a micro unevenness, a thread, or a laser. The soft tissue adhering portion 124 corresponds to a portion to which connective tissue functioning to prevent intrusion of external bacteria and to protect the bone tissues from an outside is adhered and thus, may minimize a bone loss.

Figure 5:
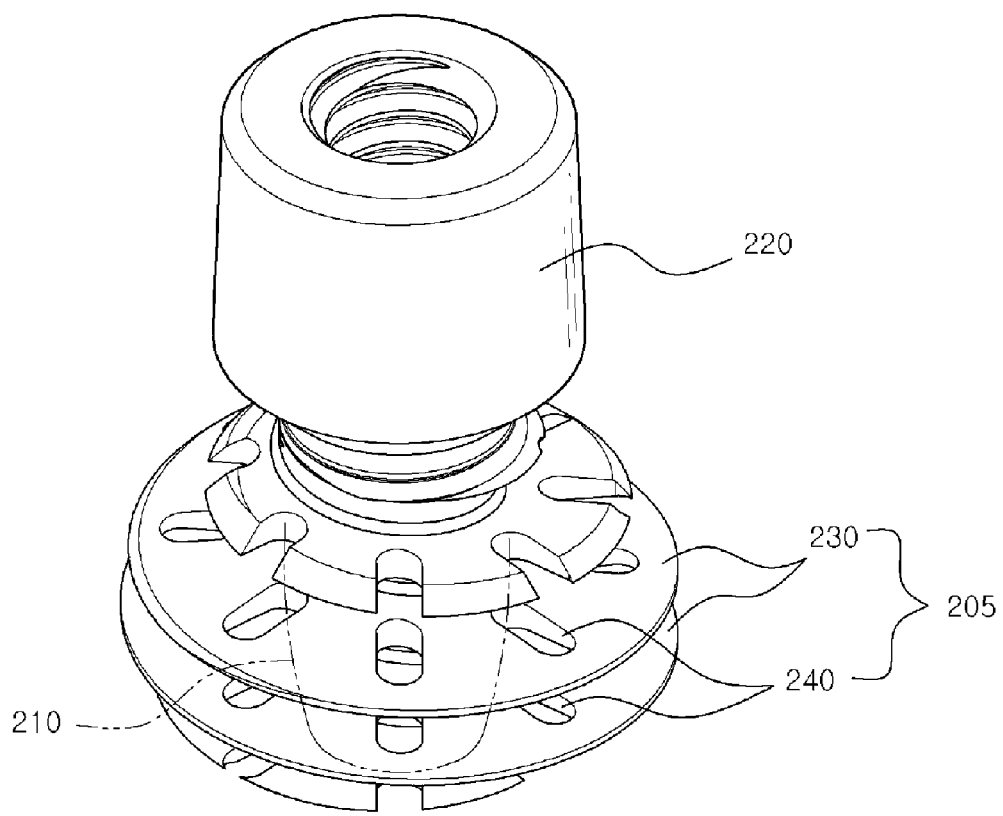
FIG. 5 is a perspective view illustrating an implant according to another embodiment of the present invention.

FIG. 5 is a perspective view illustrating an implant 200 according to another embodiment of the present invention.

Referring to FIG. 5, the implant 200 for a dental operation according to an embodiment of the present invention comprises a body portion 205 to be inserted in the bone structure and a mounting portion 220 to be positioned in a gum portion. The body portion 205 and the mounting portion 220 are integrally formed with each other and may be formed using a light metal such as titanium, zirconium, and the like. The body portion 205 includes a core 210, screw blades 230, and connecting holes 240. The mounting portion 220 includes a post to be mounted with an abutment thereon and a soft tissue adhering portion to adhere to soft tissue.

The screw blades 230 are formed from a proximal portion, an upper portion of the body portion 205, to a distal portion of the body portion 205 in the shape of a screw. The screw blades 230 may be formed to have an approximately long rectangular section, and may be formed in a direction nearly vertical to an axis of the core 210. The screw blades 230 may be formed from the proximal portion of the core 210 to the distal portion of the core 210 in the shape of the screw.

A plurality of vertically passing connecting holes 240 may be formed on the screw blades 230. The connecting holes 240 may connect an upper space and a lower space blocked by the screw blades 230. Similar to the aforementioned connecting grooves 140, the connecting holes 240 enable vertical bone tissues to partially communicate with each other and enable blood, required for healing a wound, to pass. Accordingly, it is possible to prevent necrosis of the bone tissues after implanting the implant, and to help the wounded bone tissues to be quickly recovered.

An instrument, such as a drill bit and the like, may be employed to form the connecting holes 240 in the screw blades 230, and holes may be vertically concentrically formed by the drill bit.

Bone growth factors such as BMP may be provided on the outer peripheral surface of the core 210 between the screw blades 230 and the connecting holes 240. The bone growth factors may increase the recovery speed of adjacent bone or tissues after implantation. When the bone growth factors are present in the connecting holes 240, it is possible to prevent the bone growth factors from being pushed away by the bone or tissues and thereby peeled off even during an implantation process. The bone growth factors may remain for a relatively long period of time even after implantation and function to foster the bone formation.

Although a few embodiments of the present invention have been shown and described, the present invention is not limited to the described embodiments. Instead, it would be appreciated by those skilled in the art that changes may be made to these embodiments without departing from the principles and spirit of the invention, the scope of which is defined by the claims and their equivalents.

A dental implant according to the present invention may be widely used as a structure to be implanted in bone of a living body for the purpose of treatment, for example, when mounting a prosthesis on the alveolar bone instead of a lost tooth, or when replace an articular joint of a human body.

What is claimed is:

1. A dental implant comprising:
  a body portion to be inserted in a bone structure, the body portion including a core, with a diameter of the core in a range between 1 mm and 7 mm and a length of the core between 3 mm and 10 mm, screw blades formed along an outer peripheral surface of the core in the shape of a screw, with a maximum height of the screw blades from an outer peripheral surface of the core in a range between 0.6 mm and 2.0 mm, and a thickness of a lower end portion of the screw blades between 0.25 mm and 1.5 mm, and a connecting portion in form of grooves or holes for connecting spaces blocked by the screw blades; and
  a mounting portion integrally formed on an upper portion of the core and mounted with a prosthesis thereon directly or indirectly,
  wherein a diameter of the screw blades of the body portion has a maximum diameter at an intermediate portion of the body portion, and gradually decreases as it approaches to a proximal end portion of the body portion, and the diameter of the screw blades of the body portion gradually decreases from the intermediate portion of maximum diameter to a distal end portion of the body portion, such that an outer contour of the screw blades in a cross section taken in an axial direction of the body portion has an arc or generally circular shape.

2. The dental implant of claim 1, wherein the maximum height of the screw blades from the outer peripheral surface of the core is more than one fold of the thickness of the lower end portion of the screw blade.

3. The dental implant of claim 2, wherein the maximum height of the screw blades is less than three folds of the thickness of the lower end portion of the screw blade.

4. The dental implant of claim 1, wherein the mounting portion is a frictional typed post.

5. The dental implant of claim 4, wherein a length of the mounting portion is 2 mm-7 mm at the same level as a height of gum.

6. The dental implant of claim 4, wherein a soft tissue adhering portion of 0.3 mm-2 mm width is provided between a prosthesis boundary surface of the post and an upper end of the body portion.

7. The dental implant of claim 1, wherein the mounting portion is a cement-retained typed post using a dental adhesive.

8. The dental implant of claim 1, wherein the mounting portion is a screw-retained typed post.

9. The dental implant of claim 1, wherein the connecting portion for connecting the spaces blocked by the screw blades is formed on the screw blades in the shape of a plurality of vertically-aligned grooves.

10. The dental implant of claim 1, wherein the connecting portion for connecting the spaces blocked by the screw blades is formed on the screw blades in combination of a plurality of vertically-aligned holes and grooves.

11. The dental implant of claim 1, wherein a bone growth factor is applied at the connecting portion.

12. The dental implant of claim 1, wherein a bone growth factor is applied on the outer peripheral surface of the core between the screw blades.

13. The dental implant of claim 12, wherein the dental implant is applicable to a surgical site after drilling with a drill bit, and wherein the diameter of the core applied with the bone growth factor is smaller than a diameter of the drill bit for drilling.

14. A method of implanting a dental implant for mounting a prosthesis in a bone structure of an alveolar bone, the method comprising the steps of:
providing the dental implant comprising a body portion including a core, with a diameter of the core in a range between 1 mm and 7 mm and a length of the core between 3 mm and 10 mm, screw blades formed along an outer peripheral surface of the core in the shape of a screw, with a maximum height of the screw blades from an outer peripheral surface of the core in a range between 0.6 mm and 2.0 mm, and a thickness of a lower end portion of the screw blades between 0.25 mm and 1.5 mm, wherein a diameter of the screw blades of the body portion has a maximum diameter at an intermediate portion of the body portion, and gradually decreases as it approaches to a proximal end portion of the body portion, and the diameter of the screw blades of the body portion gradually decreases from the intermediate portion of maximum diameter to a distal end portion of the body portion, such that an outer contour of the screw blades in a cross section taken in an axial direction of the body portion has an arc or generally circular shape, and a connecting portion in form of grooves or holes for connecting spaces blocked by the screw blade, and the body portion to be inserted in the bone structure, and a mounting portion integrally formed on an upper portion of the core and mounted with the prosthesis thereon directly or indirectly;
forming a drill bit hole in the bone structure of the alveolar bone in correspondence to a diameter of the core;
forming a screw groove in the bone structure of the alveolar bone in correspondence to the shape of the screw blades; and
implanting the implant in the bone structure through the drill bit hole and the screw groove.

15. The method of claim 14, wherein a bone growth factor is applied on the connecting portion before implanting the dental implant.

16. A dental implant comprising:
a body portion to be inserted in a bone structure, the body portion including a core, with a diameter of the core in a range between 1 mm and 7 mm and a length of the core between 3 mm and 10 mm, screw blades formed along an outer peripheral surface of the core in the shape of a screw, with a maximum height of the screw blades from an outer peripheral surface of the core in a range between 0.6 mm and 2.0 mm, and a thickness of a lower end portion of the screw blades between 0.25 mm and 1.5 mm, and a connecting portion in form of grooves or holes for connecting spaces blocked by the screw blades; and
a mounting portion integrally formed on an upper portion of the core and mounted with a prosthesis thereon directly or indirectly,
wherein a diameter of the screw blades of the body portion has a maximum diameter at an intermediate portion of the body portion, and gradually decreases as it approaches to a proximal end portion of the body portion, and the diameter of the screw blades of the body portion gradually decreases from the intermediate portion of maximum diameter to a distal end portion of the body portion, such that an outer contour of the screw blades in a cross section taken in an axial direction of the body portion has an arc or generally circular shape,
wherein the mounting portion has an enlarged outer diameter larger than the diameter of the core, and an inner screw hole for mounting the implant is formed only in the mounting portion without extending into the core.

17. The dental implant of claim 16, wherein the maximum height of the screw blades from the outer peripheral surface of the core is more than one fold of the thickness of the lower end portion of the screw blade, and wherein the maximum height of the screw blades is less than three folds of the thickness of the lower end portion of the screw blade.

* * * * *